United States Patent
Faulkner (12)

(10) Patent No.: US 10,570,536 B1
(45) Date of Patent: Feb. 25, 2020

(54) FILAMENT COUNT REDUCTION FOR CARBON FIBER TOW

(71) Applicant: CFA MILLS, INC., Taylorsville, NC (US)

(72) Inventor: Donald Faulkner, Taylorsville, NC (US)

(73) Assignee: CFA Mills, Inc., Taylorsville, NC (US)

( * ) Notice: Subject to any disclaimer, the term of this patent is extended or adjusted under 35 U.S.C. 154(b) by 121 days.

(21) Appl. No.: 15/810,801

(22) Filed: Nov. 13, 2017

Related U.S. Application Data

(60) Provisional application No. 62/421,550, filed on Nov. 14, 2016, provisional application No. 62/462,025, (Continued)

(51) Int. Cl.
*D02J 1/18* (2006.01)
*D02G 3/02* (2006.01)
(Continued)

(52) U.S. Cl.
CPC ............ *D02J 1/18* (2013.01); *B65H 54/2836* (2013.01); *B65H 59/08* (2013.01); *B65H 59/18* (2013.01);
(Continued)

(58) Field of Classification Search
CPC .......... D02J 1/18; D01F 9/12; B65H 54/2836; B65H 59/08; B65H 59/18; B65H 63/006;
(Continued)

(56) References Cited

U.S. PATENT DOCUMENTS

| | | | |
|---|---|---|---|
| RE23,368 E | 5/1951 | Grob et al. | 175/183 |
| 3,156,016 A * | 11/1964 | Dunlap | D02J 1/18 |
| | | | 156/166 |

(Continued)

FOREIGN PATENT DOCUMENTS

| | | | | |
|---|---|---|---|---|
| GB | 1212205 A | * 11/1970 | | D01G 99/00 |
| GB | 2108946 | 8/1982 | | D01F 9/12 |

(Continued)

OTHER PUBLICATIONS

"Customer Assistance Manual" for JointAir Yarn Splicer Code 114 &Code 115 Published by AB Carter Inc.
(Continued)

*Primary Examiner* — Khoa D Huynh
*Assistant Examiner* — Grace Huang
(74) *Attorney, Agent, or Firm* — MacCord Mason PLLC

(57) ABSTRACT

A process and apparatus for separating a carbon filament tow into a set of reduced filament count bundles. The process includes feeding a tow of carbon filaments into a guide array, mechanically splitting the tow within the guide array into filament bundles, removing a coating from the filament bundles, feeding the filament bundles into a guide pin assembly to separate the filament bundles with a reduced filament count from one another, applying a false twist to the filament bundles to loosen individual filaments then recombining the individual filaments of each filament bundle into a re-bundled ribbon. Coatings may be applied to each re-bundled ribbon prior to winding each re-bundled ribbon onto a take-up.

19 Claims, 17 Drawing Sheets

Related U.S. Application Data filed on Feb. 22, 2017, provisional application No. 62/515,899, filed on Jun. 6, 2017.

(51) Int. Cl.
| | |
|---|---|
| *D06H 3/10* | (2006.01) |
| *B65H 63/00* | (2006.01) |
| *B65H 59/18* | (2006.01) |
| *B65H 54/28* | (2006.01) |
| *G01N 27/04* | (2006.01) |
| *D01F 9/12* | (2006.01) |
| *B65H 59/08* | (2006.01) |
| *D06M 101/40* | (2006.01) |
| *D06M 15/564* | (2006.01) |
| *D06M 15/71* | (2006.01) |
| *D02G 3/28* | (2006.01) |

(52) U.S. Cl.
CPC ............ *B65H 63/006* (2013.01); *D01F 9/12* (2013.01); *D02G 3/02* (2013.01); *D02G 3/281* (2013.01); *D06H 3/10* (2013.01); *D06M 15/564* (2013.01); *D06M 15/71* (2013.01); *G01N 27/041* (2013.01); *D06M 2101/40* (2013.01); *D10B 2101/12* (2013.01)

(58) Field of Classification Search
CPC ............ D06M 15/564; D06M 15/71; D06M 2101/40; G01N 27/041; D02G 3/02; D02G 3/281; D02G 1/04; D06H 3/10; D10B 2101/12; D01G 1/04; D01G 15/66; D01H 1/11
USPC ............................................ 57/243, 2.3, 2.5
See application file for complete search history.

(56) References Cited

U.S. PATENT DOCUMENTS

| | | | | |
|---|---|---|---|---|
| 3,294,326 | A | 12/1966 | Raasch | |
| 3,417,560 | A * | 12/1968 | Watson | D04H 3/00 57/2 |
| 3,669,552 | A * | 6/1972 | Briscoe | G01N 33/365 356/429 |
| 3,677,484 | A * | 7/1972 | Yazawa | B29O 53/32 242/520 |
| 3,704,485 | A * | 12/1972 | Hall | D02J 1/18 28/283 |
| 3,800,160 | A * | 3/1974 | Ishizawa | G01N 33/365 377/6 |
| 3,951,321 | A * | 4/1976 | Heusser | B65H 51/10 226/97.4 |
| 4,004,406 | A * | 1/1977 | Suzuki | D01H 1/115 57/200 |
| 4,077,822 | A | 3/1978 | Logwin | 156/157 |
| 4,122,703 | A | 10/1978 | Davis | 73/37 |
| 4,130,679 | A | 12/1978 | Breznak et al. | 428/58 |
| 4,137,699 | A * | 2/1979 | Stahlecker | B65H 63/00 57/263 |
| 4,397,137 | A | 8/1983 | Davies et al. | 57/22 |
| 4,428,992 | A | 1/1984 | Street | 428/114 |
| 4,476,173 | A | 10/1984 | Bachmann et al. | 428/57 |
| 4,539,802 | A | 9/1985 | Bertoli et al. | 57/22 |
| 4,617,716 | A | 10/1986 | Lay et al. | 29/526 |
| 4,660,365 | A | 4/1987 | Raasch | 57/263 |
| 4,733,829 | A | 3/1988 | Mima | 242/35.6 |
| 4,735,693 | A | 4/1988 | Asai et al. | 204/1 T |
| 4,803,762 | A | 2/1989 | Sheehan | 28/104 |
| 4,897,286 | A | 1/1990 | Kosuda et al. | 427/44 |
| 4,923,637 | A | 5/1990 | Yagi et al. | 252/511 |
| 4,947,635 | A | 8/1990 | Speranzin et al. | 57/202 |
| 5,054,173 | A * | 10/1991 | Schafer | D02G 1/127 28/263 |
| 5,078,840 | A | 1/1992 | Ogawa et al. | 204/130 |
| 5,140,852 | A * | 8/1992 | Bonigk | D02G 1/161 250/559.08 |
| 5,217,778 | A * | 6/1993 | LaCasse | F16D 69/026 188/251 A |
| 5,528,155 | A | 6/1996 | King et al. | 324/713 |
| 5,619,848 | A | 4/1997 | Costales et al. | 57/261 |
| 5,832,709 | A | 11/1998 | Lassmann et al. | 57/263 |
| 6,039,281 | A | 3/2000 | Badiali et al. | 242/475.5 |
| 6,195,975 | B1 | 3/2001 | Hand et al. | 57/293 |
| 6,258,304 | B1 * | 7/2001 | Bahia | C08J 5/18 264/171.1 |
| 6,339,921 | B1 | 1/2002 | Lassmann et al. | 57/264 |
| 6,375,875 | B1 | 4/2002 | Paulauskas et al. | 264/29.2 |
| 6,385,828 | B1 * | 5/2002 | Kiss | D02J 1/18 19/65 T |
| 6,485,592 | B1 | 11/2002 | Yoshimura et al. | 156/148 |
| 6,526,739 | B2 * | 3/2003 | Kutsenko | D01D 5/096 57/296 |
| 6,561,019 | B1 | 5/2003 | Kossat et al. | 73/160 |
| 6,742,560 | B2 | 6/2004 | Takeuchi et al. | 156/433 |
| 6,938,849 | B2 | 9/2005 | Badiali | 242/475.5 |
| 7,155,890 | B2 | 1/2007 | Kawamura et al. | 57/22 |
| 7,941,903 | B2 | 5/2011 | Ikeda et al. | 28/271 |
| 8,124,228 | B2 | 2/2012 | Yoshikawa et al. | 428/367 |
| 8,129,017 | B2 | 3/2012 | Yoshikawa et al. | 428/367 |
| 8,505,271 | B2 | 8/2013 | Bowland et al. | 57/22 |
| 8,530,861 | B1 | 9/2013 | Anderson et al. | 250/459.1 |
| 8,603,620 | B2 | 12/2013 | Hitoe et al. | 428/292.1 |
| 9,528,197 | B2 | 12/2016 | Naskar | 9/21 |
| 2004/0168425 | A1 | 9/2004 | Kawamura et al. | 57/22 |
| 2012/0321888 | A1 | 12/2012 | Rumy et al. | 428/367 |
| 2015/0147543 | A1 | 5/2015 | Guha et al. | 428/213 |
| 2017/0037545 | A1 * | 2/2017 | Keppel | D02J 1/18 |
| 2018/0043580 | A1 * | 2/2018 | Prins | B29B 15/14 |
| 2019/0136421 | A1 * | 5/2019 | Masuda | D02G 3/34 |
| 2019/0263625 | A1 * | 8/2019 | Motohashi | D06H 7/02 |

FOREIGN PATENT DOCUMENTS

| | | | |
|---|---|---|---|
| GB | 2340136 | 2/2000 | |
| JP | 54/55624 | 5/1979 | ............ D01F 9/14 |
| JP | 58/208420 | 12/1983 | ............ D01F 9/12 |
| JP | 2004/100132 | 4/2004 | |
| WO | 2001/090458 | 5/2001 | ............ D02G 1/04 |
| WO | WO-2016162136 A1 * | 10/2016 | .......... B65H 51/005 |

OTHER PUBLICATIONS

"Splice Scanner III" Portable Yarn Strength Tester Mesdan Lab p. 1-2 Company With Management System Certified by DNV.

"Strain sensing Using Carbon Fiber" J. Mater. Res., vol. 14, No. 3, Mar. 1999, Wang et al.

* cited by examiner

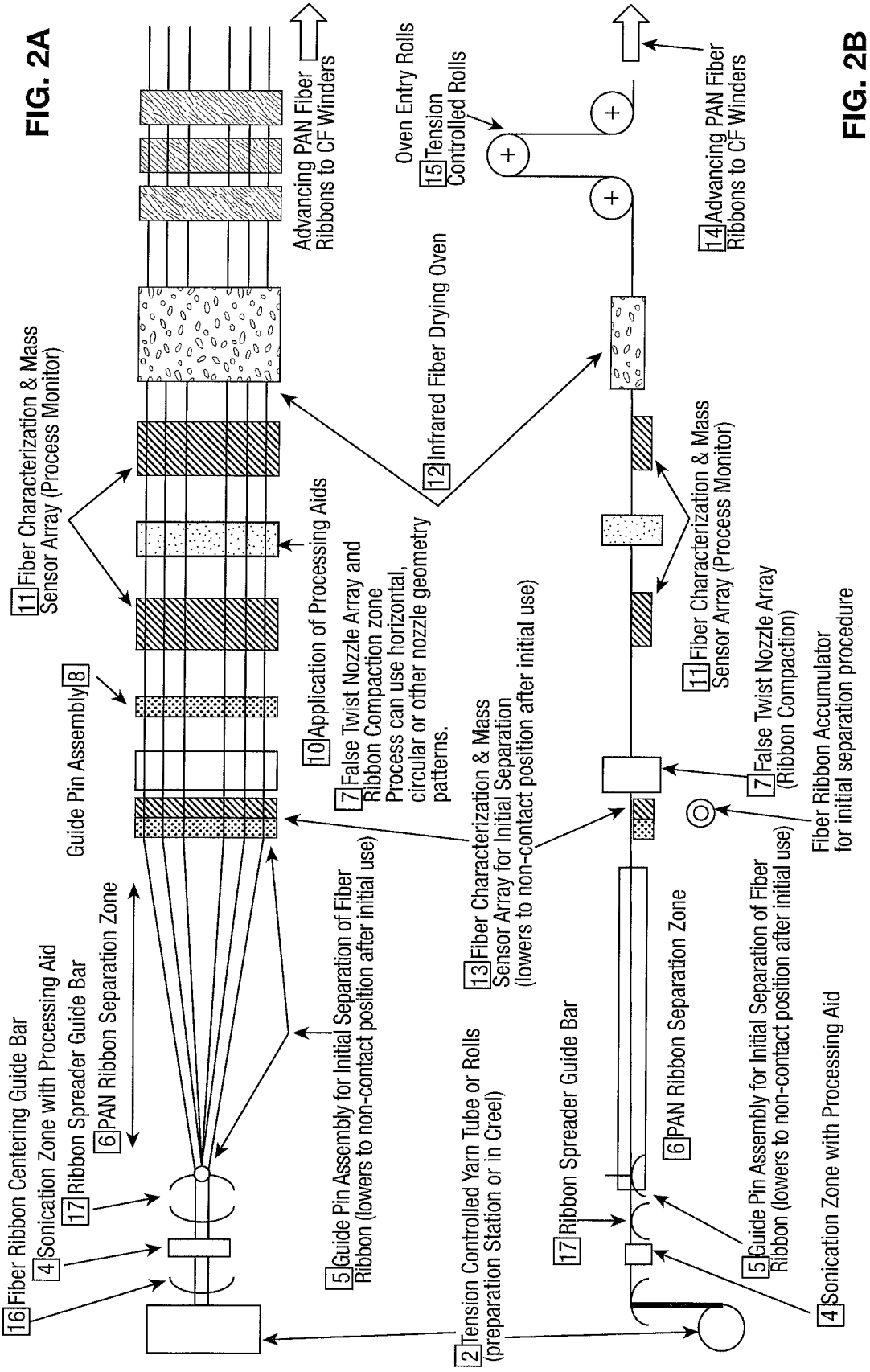

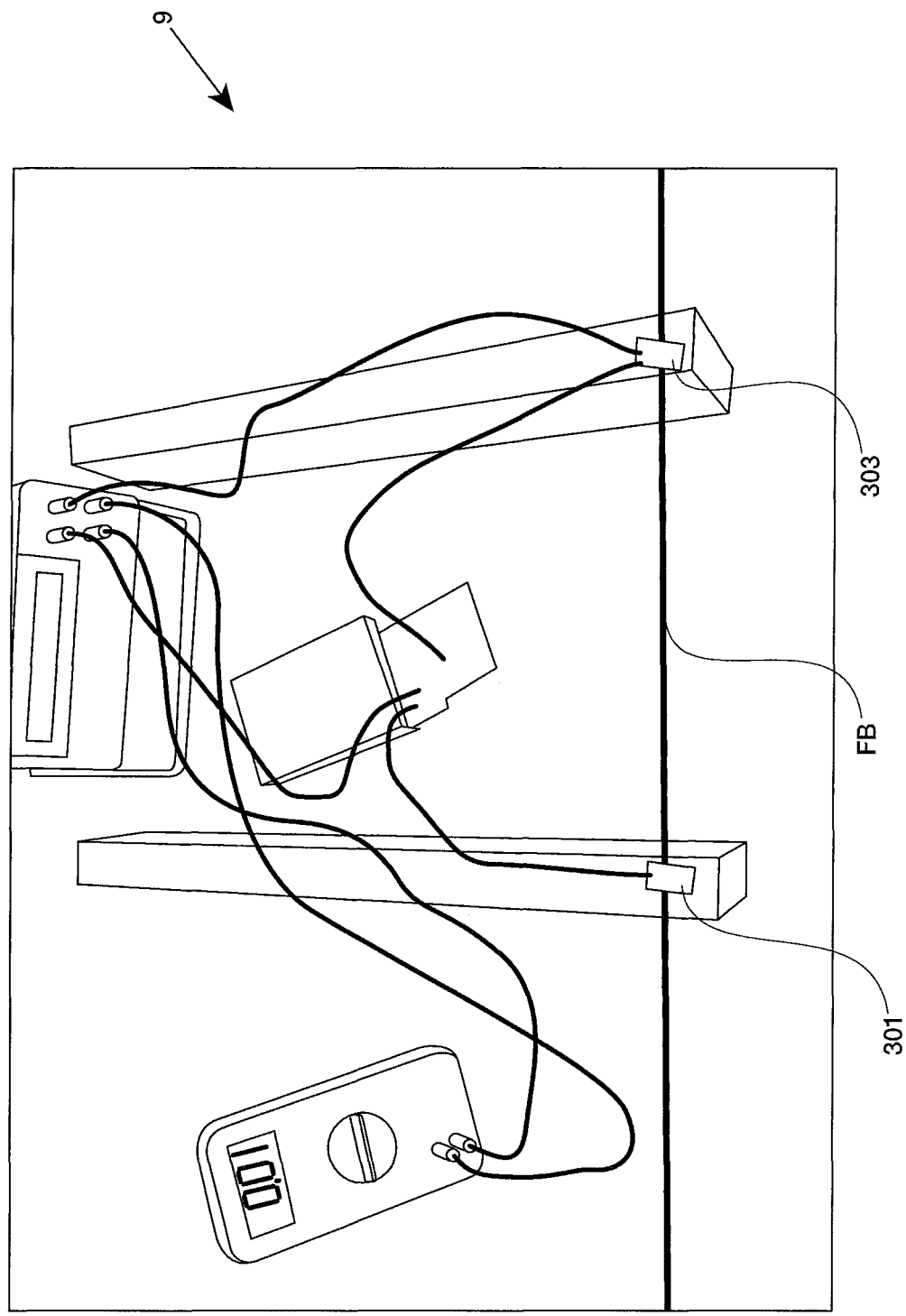

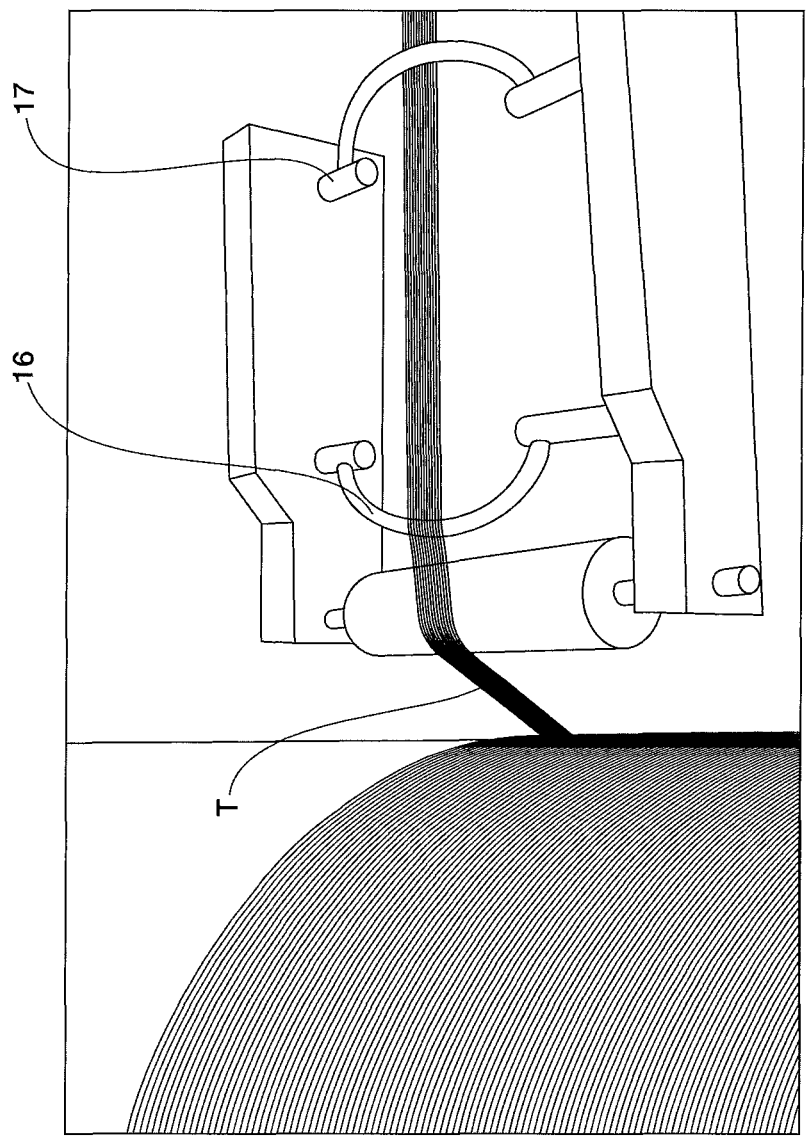

FILAMENT COUNT REDUCTION FOR CARBON FIBER TOW

This application claims the benefit of Provisional Patent Application 62/421,550 filed Nov. 14, 2016, Provisional Patent Application 62/462,025 filed Feb. 22, 2017, and Provisional Patent Application 62/515,899 filed Jun. 6, 2017.

BACKGROUND OF THE INVENTION

Carbon fibers are produced from polymers such as polyacrylonitrile (PAN) and are employed in a wide variety of applications due to their conductivity, strength, and low weight. For example, carbon fibers are commonly incorporated with polymers to form lightweight rigid materials often used in the aerospace and automotive industries. Carbon fibers may also be used in textiles to weave fabric incorporating desirable properties of carbon fibers while also providing a unique look.

One of the main drawbacks of using carbon fibers is its high expense. There remains a need within the industry to lower the costs of carbon fiber production without compromising its structural integrity. A recent advance by Oak Ridge National Laboratories has succeeded in producing a 12,000 filament tow at a cost less than prior production methods. But tows of 12,000 filaments are too large for many applications and wasteful for others. Applicants' invention aims to fulfill this need by providing a method and apparatus for splitting a ribbon from a carbon filament tow into multiple filament bundles having a reduced filament count to provide a cheaper alternative compared to standalone carbon filament tows having the same filament count.

SUMMARY OF THE INVENTION

The present invention is directed towards a method and apparatus for separating a carbon filament tow into reduced filament count bundles. The following steps may be performed in either a continuous or discontinuous process. A bundle of carbon filaments (typically from a 12K carbon tow) is fed into a set-up guide array using rollers to maintain constant tension in the ribbon. The filaments traverse a path during the process, enabling volume processing. As the ribbon is fed into the guide array, the ribbon is mechanically split into a plurality of separate filament bundles. The guide array may comprise a set of rotating metal, polymer, or ceramic rollers/pins each having a groove for the separate filament bundles to wrap around. The ceramic rollers (or pins) may also be useful for reducing vibration of the feed and the induced oscillation of the false twist nozzle. The filaments traverse a path during the process, enabling volume processing of the entirety of the ribbon.

The guide array is used for an initial separation that is an approximation. Filament bundle sensors are used to determine the number of filaments in each reduced bundle. A needle-type device can be used to transfer filaments from bundles that are too large to bundles that are too small, to achieve equalization. When the filament bundle sensor detects deviations from equal (or other desired size) bundles, the needle-type device is re-deployed to correct back to equalized (or other desired size) bundles.

At various stages during the process, filament sensors may be employed to verify the integrity of the filament count of the filament bundles. In one example, the filament sensor may comprise measuring an optical signal on the filament bundle, wherein fluorescence at a particular spectrum indicates the filament bundle's integrity. Fluorescent particles may also be applied as an intermittent filament coating regularly adhered to the filaments, so the intensity of the fluorescence is a measure of the filament count.

As another example, the filament sensor may verify the filament count by measuring the electrical resistance of the tow or bundle of carbon filaments. In one embodiment, the filament sensor may comprise a power source configured to apply a current to a segment of the tow or bundle of carbon filaments and a data acquisition system. The data acquisition system includes a first electrode contacting the advancing tow or bundle of carbon filaments at a first point and a second electrode contacting the advancing tow or bundle of carbon filaments at a second point spaced apart from the first point. The data acquisition system is configured to measure the voltage drop across the segment of the tow or bundle of carbon filaments between the first and second points when a current is applied. The resistance of the tow or bundle is calculated by dividing the current applied by the power source into the voltage measured by the data acquisition system. A decreased resistance indicates a higher count of filaments in the tow or bundle of carbon filaments, while an increased resistance indicates a lower count of filaments in the tow or bundle of carbon filaments. This sensor step can be used to detect whether filaments have been diverted from one divided bundle to the other, so filaments from the high-count bundle can be directed by a tool to a low-count bundle.

Downstream of the guide array and upstream of the false twister, processing aids may be applied to remove ribbon coatings (originally applied to maintain bundle cohesion) and thereby facilitate dissociation. Typically, thermoplastic polyurethane (TPU) coatings are removed from the filament bundles using ultrasonic low sonication as the bundle traverses a liquid bath at this stage. The coatings used on the ribbon may vary by manufacturer and therefore the processing aids applied may also differ. The coatings do not have to be entirely stripped from the filaments; just enough to unstick or dissociate the filaments from one another in the bundles.

The dissociated filament bundles are then fed into a guide pin assembly that uses spreaders to segregate the separate filament bundles into the desired filament count. The pattern for the spreaders used may vary; for instance, the spreaders can be arranged in a rectangular or circular pattern. As the filament bundles advance through the guide pin assembly, some of the excess liquid (if any) from the processing aids is wiped away. Once the separated bundles pass though the false twist nozzle assembly and can be removed from fiber contact, the guide pin assembly is no longer required to maintain the filament dissociation process. The three-dimensional disassociation of the filaments into discrete lower filament count bundles, once established, is dynamically controlled by a combination of spreader guide configuration, the false twisting actions, downstream fiber path geometry and the precisely controlled fiber ribbon tension created by the upstream and downstream rolls. The three-dimensional disassociation that occurs in the separation zone may occur without additional guide contact prior to the false twist nozzle array. A grooved guide roller guide may be located upstream in local proximity to the false twist nozzle array but not encroaching into the separation zone. The positioning of the false-twister induced vibrational patterns may also facilitate separation.

The separate filament bundles advance into a pneumatic false-twist nozzle array. Each nozzle agitates the filaments slightly, to aid in their separation from the initial large bundle and into the smaller, desired bundles and to recombine the filaments of each smaller filament bundle into a ribbon. The false twist nozzle produces twists at a frequency up to 100 Hz and utilizes the linear inter-filament friction of the filaments as a mechanism for re-bundling the filaments into a ribbon. Preferably, each nozzle imparts a false twist in a direction opposite its next-adjacent nozzle. Thus the adjacent ribbons are false-twisted differently from one another, helping the physical separation of the filaments of the ribbons from their adjacent ribbons.

Processing aids may then be applied to each ribbon using an advanced finish nozzle (AFN). These processing aids are used to further maintain bundle cohesion, and may comprise coatings currently used in the market such as TPU. At this stage, other particles may also be applied to the ribbons, such as markers for source identification. Coatings may be cured by feeding the ribbons through an IR heating oven.

Once the processing aids are applied, the ribbons are then wound onto their respective take-up using filament ribbon winders. Use of a circular aperture provides continuous contact and support for the fiber bundle and also helps to reduce tension spikes in the advancing filament bundles. Factors such as the helix angle and winding tension can be modified as the ribbon is wound.

BRIEF DESCRIPTION OF THE DRAWINGS

FIG. 1B is a front view of a circular array of false twist nozzles in for a continuous carbon fiber ribbon (CFRS) separator;

FIG. 1C is a front view of another pattern of false twist nozzles in for continuous carbon fiber ribbon (CFRS) separator;

FIG. 2A is a plan schematic view of continuous carbon fiber ribbon (CFRS) separator and process according to another embodiment;

FIG. 2B is a side view of the embodiment of FIG. 2A;

FIG. 6A is an overhead view of a fiber sensor for measuring electrical resistance and its effect on the filaments;

FIG. 9 is a perspective view of a bar that can be mounted to serve as a centering guide bar or a spreader guide bar;

DETAILED DESCRIPTION OF EXAMPLES OF THE INVENTION

Figure 1A:
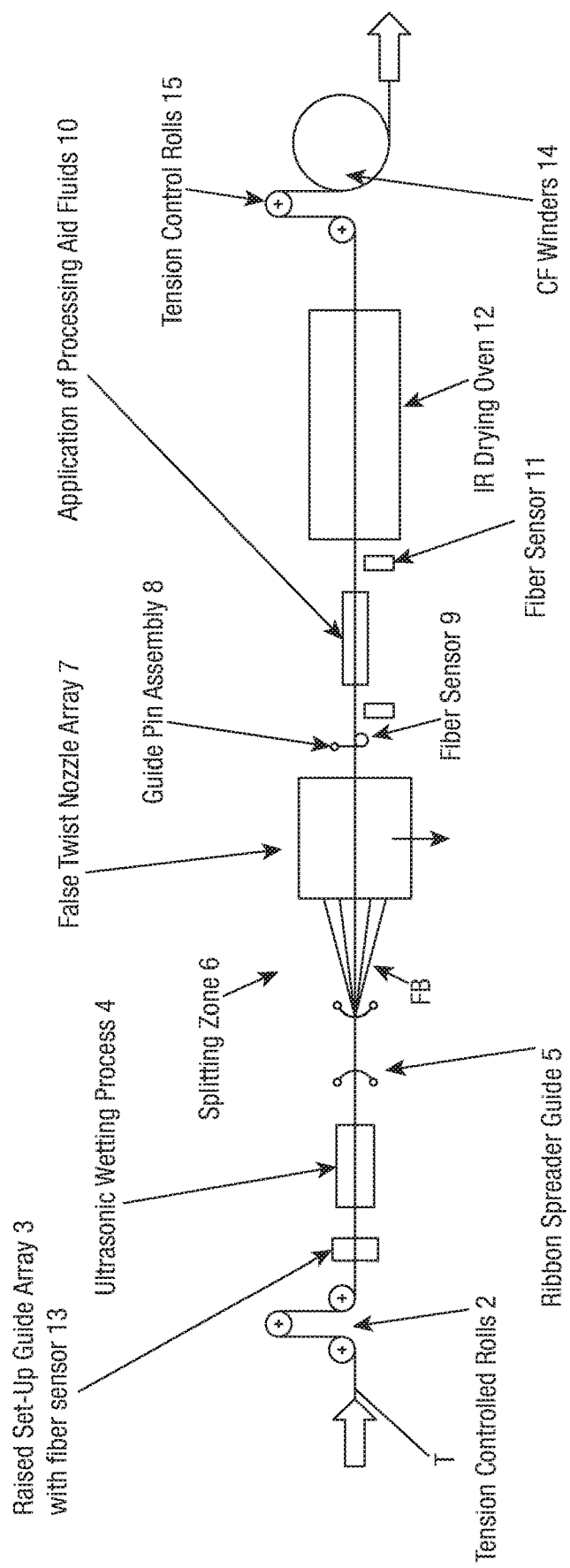
FIG. 1A is an overview of a continuous carbon fiber ribbon (CFRS) separator and process according to one embodiment.

FIG. 1A shows a diagram of a carbon fiber ribbon splitting (CFRS) apparatus. In one embodiment, the apparatus includes a set-up guide array 3 with a set of tension control rollers 2 for maintaining a controlled tension on a tow T of carbon filaments with a first filament count feeding into the set-up guide array 3. The tow of carbon filaments are initially split within the set up guide array (rotating grooved roller guide) 3 to create a plurality of filament bundles with a reduced filament count.

This splitting is initially accomplished mechanically with a guide array 3. Once the ribbon is initially split, the guide array 3 is removed from fiber contact due to the high incidence of broken filaments associated with the direct mechanical separation. The types of grooved guide rollers may vary to provide flexibility in production. In another embodiment, a spreader guide bar 17 as shown in FIG. 2 and FIG. 9 may be included to facilitate mechanical separation of the ribbon by applying tension to the ribbon and spreading the ribbon. The spreader guide bar 17 may comprise an arch shape, wherein the ribbon advances substantially along the center on top of the arch. A complimentary U-shaped guide bar 16 may be placed upstream of the spreader guide bar 17 to center the ribbon and maintain tension on the advancing ribbon.

Precise tension control of the advancing carbon fiber ribbon is helpful to assist in the separation dynamic element of the process. This is accomplished by the use of one or more electronic tension controlled rolls 2 to isolate the advancing carbon fiber ribbon from upstream tension variations. A nip roll may also help prevent slippage. Complementary tension control rolls 15 at the end of the process maintain the tension in cooperation with the rolls 2. Upstream and downstream rolls or take-up winders may be used. Highly accurate tension control of the advancing fiber ribbons facilitates take-up winding or entry into other processing steps. As seen in the embodiment shown in FIG. 2, a centering guide bar 16 may also be included to center the ribbon for entry into the set-up guide array 3. The centering guide bar 16 may comprise a U-shape, wherein the ribbon advances substantially along the center within the U-shaped guide bar.

Typically, the initial carbon fiber tows used herein have been processed with a coating to maintain bundle cohesion and increase its resin compatibility. Resin compatibility enables the carbon fiber ribbon to bind to other polymers. For example, thermoset polyurethane (TPU) may have been applied to the carbon fiber ribbon to maintain bundle cohesion and additional ligands may be applied with the TPU to increase resin compatibility as is known in the art. In another example, atmospheric plasma etching of an exposed surface of the carbon fiber ribbon may be performed to increase its wettability.

Any coatings (or similar treatments) applied to the initial carbon fiber may be removed or reduced from the filament bundles to facilitate dissociation during the process using processing aids. Processing aids may comprise fluids that weaken or remove binding particles attached to the carbon fiber that were initially used by its manufacturer to promote ribbon integrity. The processing aid may include a low amount of lubricant, typically less than 1% and no greater than about 2%. For some carbon fiber tows, the lubricant may already be applied by its manufacturer. Application of a processing aid (aqueous or solvent based) 4 to the filament bundle and ultrasonic low sonication is used to facilitate the filament dissociation using the sonication of a processing liquid. This process may require multiple sonication zones with discrete processing aids; for example, one zone to remove a previously applied coating, and another zone to subsequently add one or more other processing aids for other purposes. The liquid processing aids are temporarily attached to the advancing fiber ribbon as an adhered boundary layer. The surrounding processing liquid is used to deliver the desired ultrasonic agitation of the liquid and fiber ribbon.

In some embodiments, the apparatus may further include a spreader guide pin assembly 5. Once the tow T has been split, the filament bundles FB may be fed into the spreader guide pin assembly 5 to center and mechanically spread the advancing carbon fiber ribbon for the three dimensional disassociation of the filaments into separate filament bundles FB of the desired filament count. The guide pin assembly 5 may also remove excess liquid entrained on the filaments bundles from the coating removal process.

Figure 12:
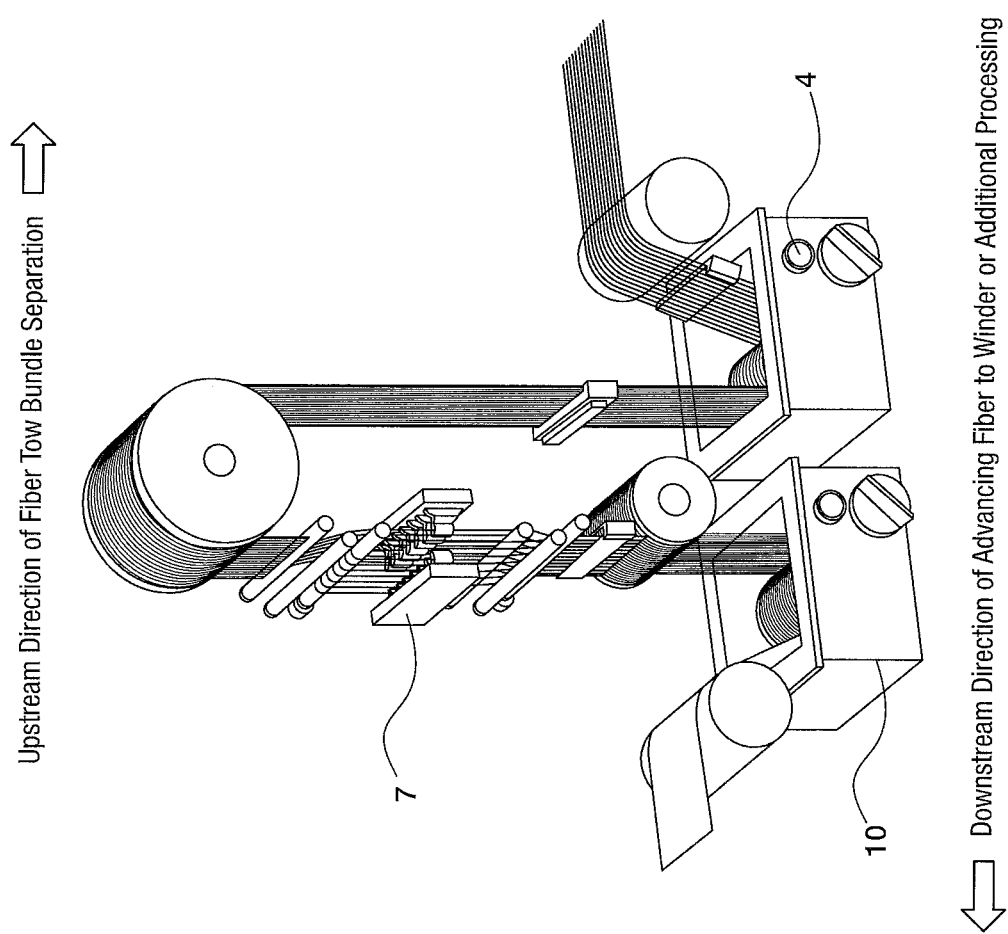
FIG. 12 is an enlarged view of multiple sonication zones and the false twist nozzle array arranged in between the two zones.

False twists may be applied to the filament bundles to further loosen the individual filaments from one another. As seen in FIGS. 1A and 2, the apparatus may further include a pneumatic false twist nozzle array 7 to dissociate the filaments and recombine the separate filament bundles into a re-bundled ribbon using the linear inter-filament friction of the individual filaments. Each of the reduced size bundles passes through one of the nozzles. As seen in FIG. 12, the false twist nozzle array 7 may be arranged between sonication zones to receive the filament bundles after a previously applied coating is removed from the first zone 4, and to direct the filament bundles to the second zone 10 for the application of one or more other processing aids for other purposes.

Figure 3A:
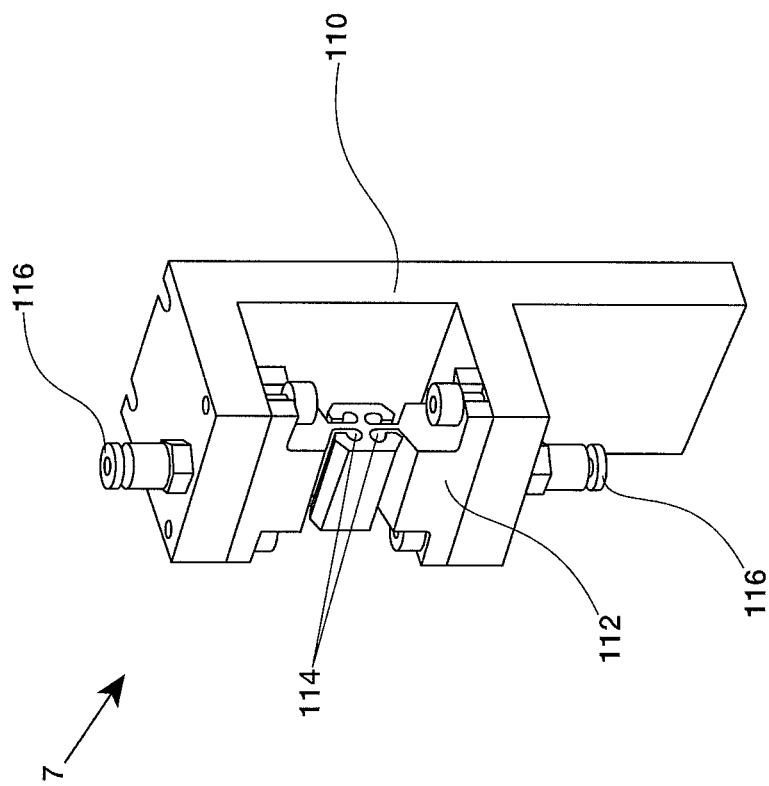
FIG. 3A is a top perspective view of one embodiment of a modular false twist nozzle quad type for use in carbon fiber bundle/ribbon splitting.
Figure 3B:
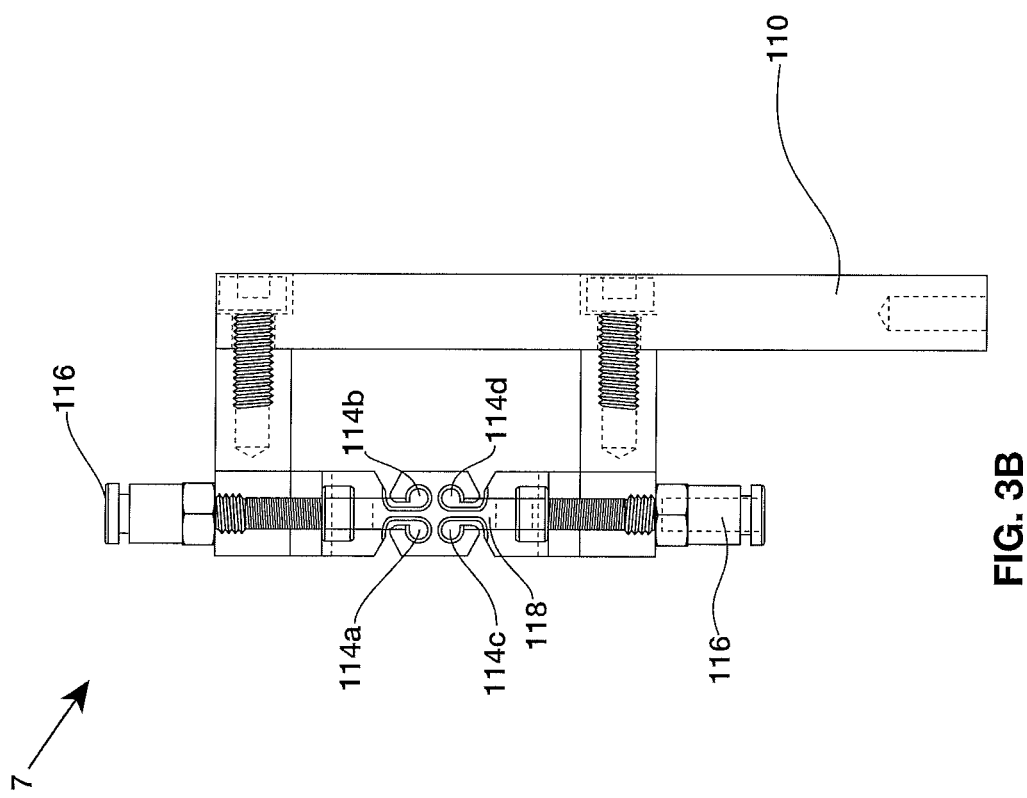
FIG. 3B is a sectional view of the false twist nozzle of FIG. 3A.

The false twist nozzle array(s) 7 can be arranged in a linear pattern, circular pattern (See FIG. 1B) or a more complex geometry pattern (See FIG. 1C) as dictated by the process requirements for the number of fiber ribbons and their filament count ranges. FIGS. 3A and 3B provide one example of a modular false twist nozzle array in which the four nozzles are arranged in a square. The pneumatic false-twist nozzle array assists in the loosening of individual filaments or groups of filaments upstream of the pneumatic false-twist array 7 and the subsequent recombining of the filaments into a re-bundled ribbon FB by producing S and Z twists on the separating filament bundles. The accumulation of actual twist in the subtow fiber bundles is zero and therefore typically avoids deleterious filament mixing that may interfere with the exothermic needs of the process for highly uniform heating. Preferably, each nozzle imparts a false twist in a direction opposite its next-adjacent nozzle. Thus the adjacent ribbons are false-twisted differently from one another, helping the physical separation of the filaments of the ribbons from their adjacent ribbons.

As seen in FIGS. 3A and 3B, a support 110 holds the false twist nozzle assembly, which is made up of a housing with four channels 114, one for each of the separated filament bundles to pass through. Pressurized air inlets 116 connect via passageways 118 to the channels 114 to inject air tangentially into each channel. The resulting rotary motion of the air in the channels 114 twists the filaments in a false twist fashion, sending twists upstream to the ribbon spreading guide 5 and imposing an oscillation on the filaments that tends to loosen them from one another, enabling the original tow to separate into the desired reduced-filament count bundles FB. For example, channels 114a and 114d may be configured to rotate the filament bundle in a clockwise direction while channels 114b and 114c are configured to rotate the filament bundle in a counterclockwise direction. Rotating the filament bundles in opposing directions while the filament bundles advance downstream enables easier dissociation of the ribbon and filament bundles upstream of the false-twist array 7. Otherwise, dissociation of the ribbon and filament bundles becomes difficult and increases the risk that the carbon filaments will snag or break during the separation process. Application of the twists by the false twist nozzle array 7 creates a tension in the filament bundle upstream of the nozzle array 7, and resistance of the twist by the ribbon upstream may facilitate its dissociation downstream.

Figure 4:
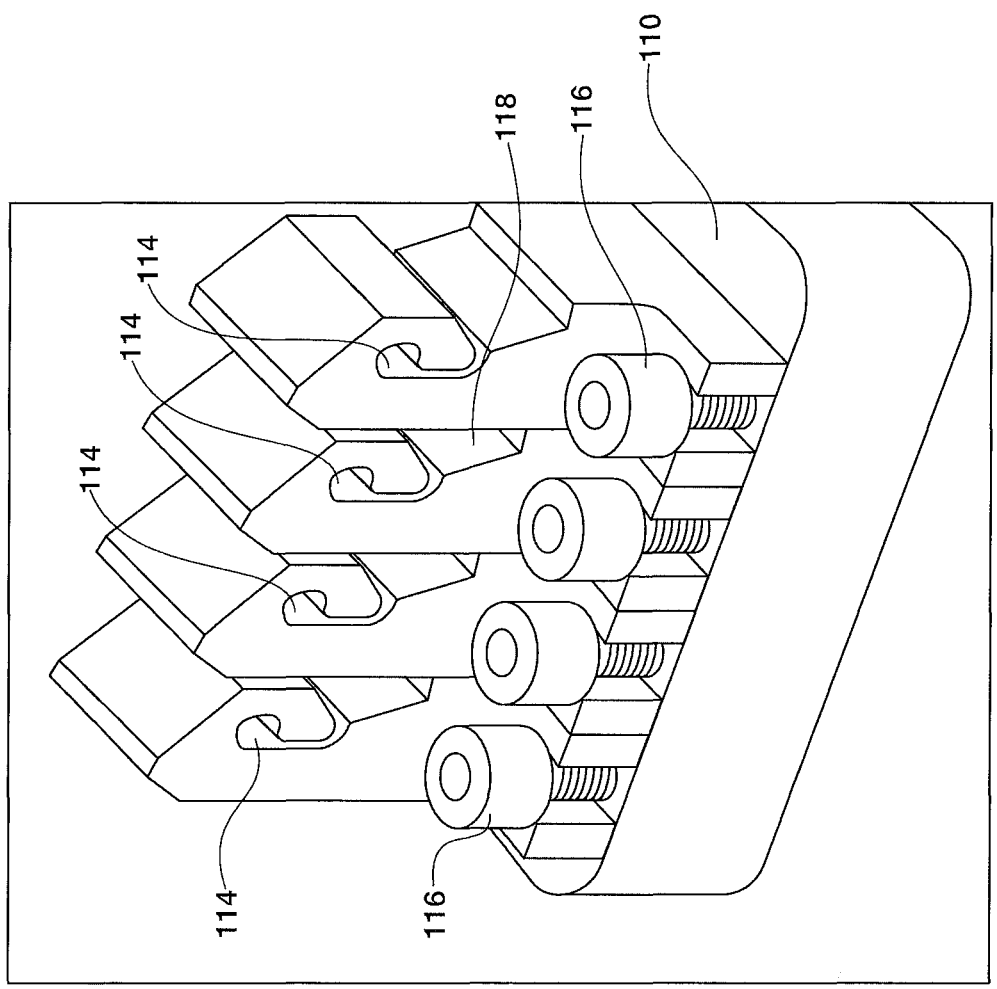
FIG. 4 is a top perspective view of another embodiment of a modular false twist nozzle quad type for use in carbon fiber bundle/ribbon splitting.

FIG. 4 depicts another example of a false twist nozzle array.

Figure 5:
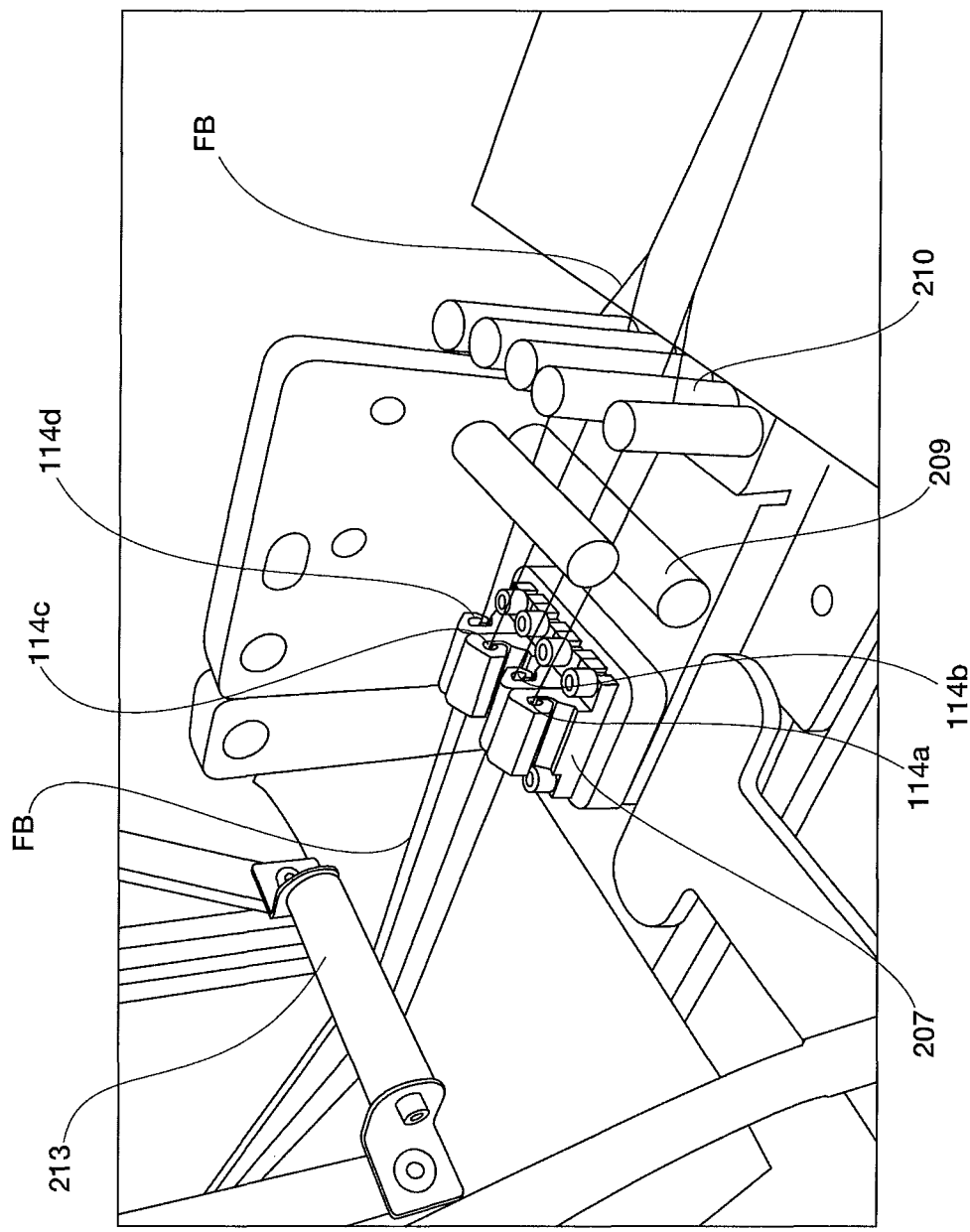
FIG. 5 is a schematic of another false twist nozzle array and its effect on the filaments.

FIG. 5 shows a different false twist nozzle assembly 207, in which the four channels 114 are arrayed horizontally and all supplied with pressurized air from below. Each channel 114 in the embodiment shown has an aperture size of approximately 3 mm in diameter. Channels 114a and 114c are configured to rotate the filament bundle in a clockwise direction while channels 114b and 114d are configured to rotate the filament bundle in a counterclockwise direction. The separated filament bundles FB can be seen extending downstream to the left of the assembly 207, and approaching from upstream to the right. As the filament bundles advance downstream from right to left, the tension applied by the nozzle array 7 travels upstream in the opposing direction.

Figure 10A:
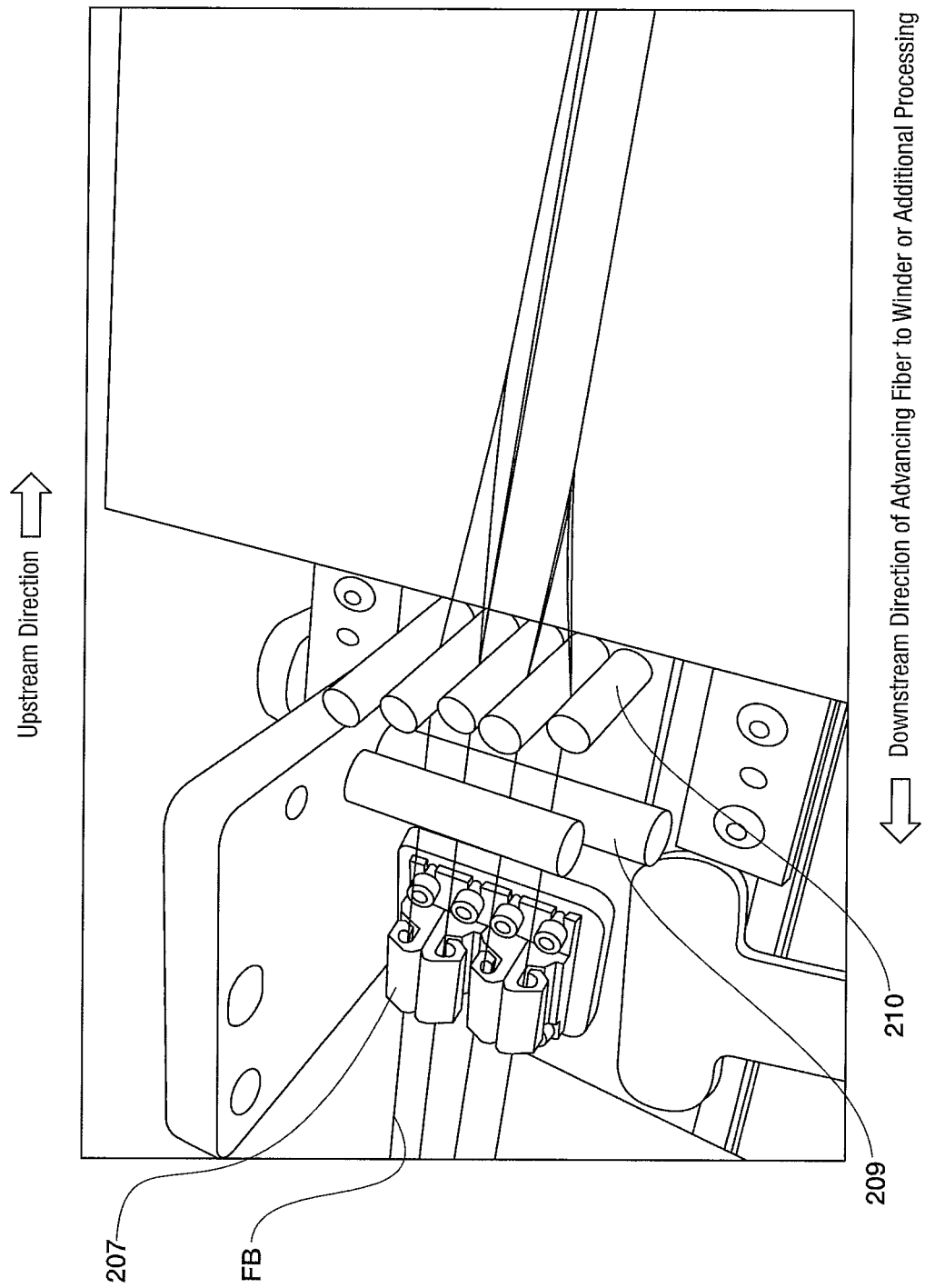
FIG. 10A is a perspective view of the false twist nozzle array.
Figure 10B:
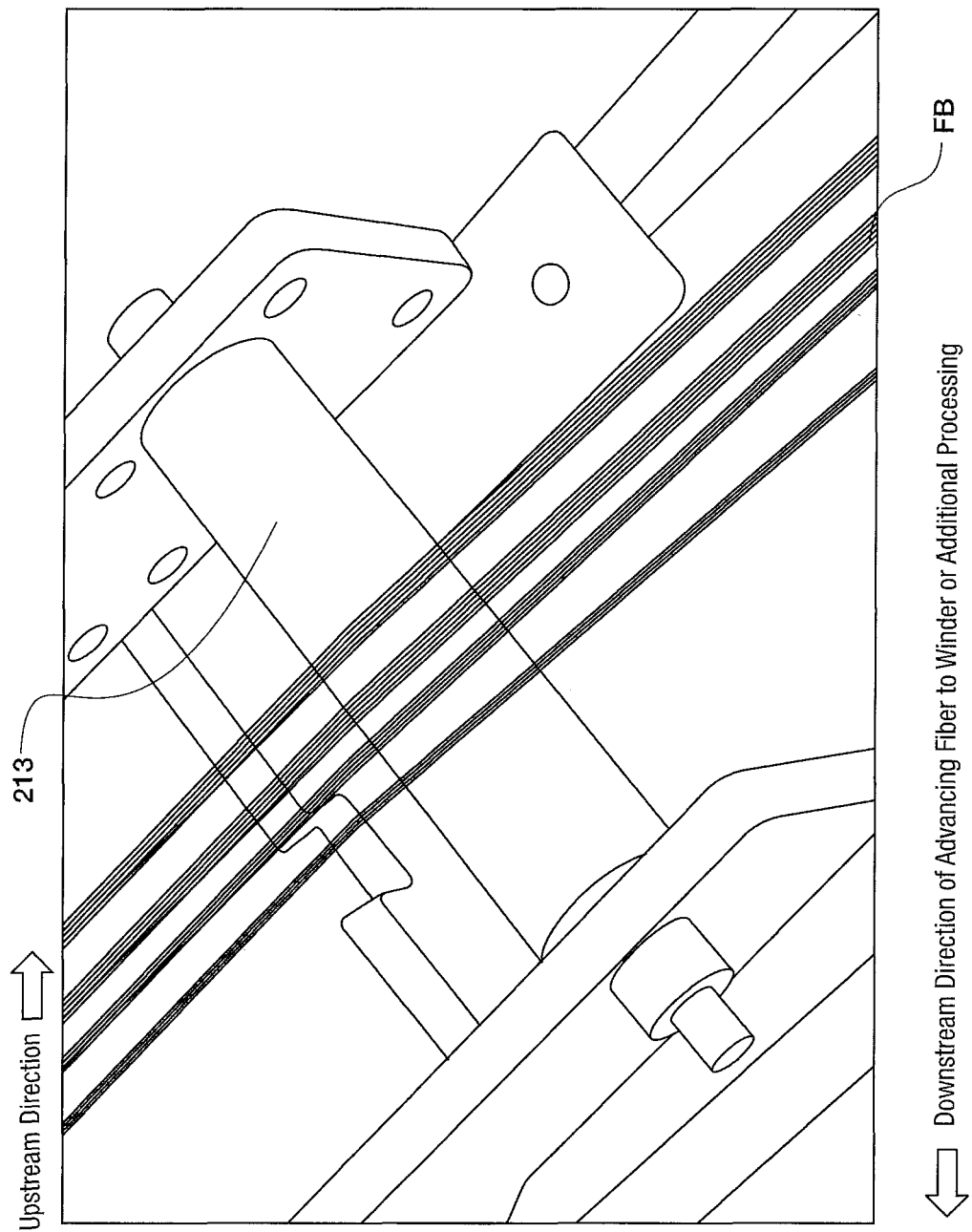
FIG. 10B is a perspective view of the ribbon spreader.
Figure 11:
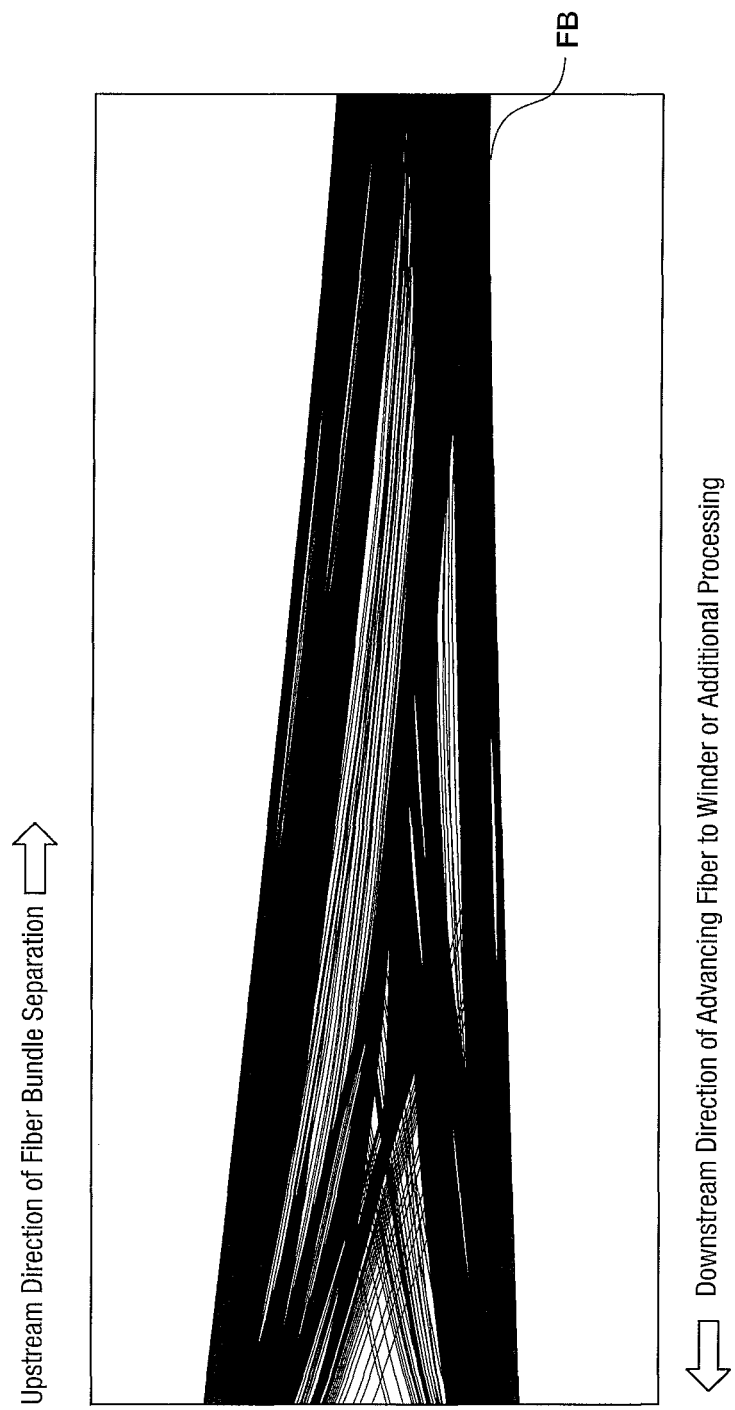
FIG. 11 is an enlarged view of the filament bundles advancing downstream into the false twist nozzle array and dissociating into subtow bundles.

The filament bundles FB to the right are segregated by the ribbon spreader 210, and as can be seen in FIGS. 10A, 10B and 11, the four filament bundles themselves separate from two intermediate filament bundles as the oscillations in the filaments work their way upstream. The false twist nozzle array induces an upstream/downstream composite interaction, where oscillations facilitate dissociation of the filaments upstream into subtow bundles, and also facilitates reassembly of the fiber bundles advancing downstream. The spacing between the pins of the ribbon spreader 210 may vary depending on the size of the advancing filament bundles. For splitting a 12K carbon fiber tow, the spacing may be between about 1 mm to about 2 mm. Guide pins 209, 213 help to assure that the filament bundles are coplanar with the channels 114 through the false twist nozzle assembly 207.

The pneumatic false twist nozzle array 7 provides S/Z (or Z/S) false twist frequencies up to 100 Hertz and is suitable for tow speeds in excess of 8 meters per minute. The tow speed, tension, and filament count also influence the S/Z false twist dynamic. The false twist action has been observed to produce a suitable ribbon for post carbonization processes including fabric formation techniques such as weaving or braiding applications. Selections of tow speed, tension and filament count can be varied to achieve optimum results within the scope of this invention.

The S/Z false twist nozzle array 7 provides additional multi-dimensional kinetic energy to the advancing fiber ribbon to disassociate advancing filaments from adjacent or near fiber ribbons for inclusion in the requisite fiber ribbon FB. The S/Z false twist action 7 subsequently recombines the filaments into a loosely cohesive flat fiber ribbon FB suitable for post processes (i.e. weaving, braiding etc.).

As seen in FIGS. 1 and 2, spacing 6 provides suitable space and distance between the guide pin assembly 5 and the pneumatic false twist nozzle array 7 for the dissociation (splitting) of the advancing tow or bundle of filaments. In some embodiments, the set-up guide array 3 can be separated from the ribbon once the apparatus is in operation so that the filaments loosened by the false twist nozzle array follow separate paths through the spreader guide pin assembly 5 in their respective filament bundles. If the infeed supply of tow T is essentially endless, the set-up guide array 3 can be removed more-or-less permanently, allowing the separation caused by the false twist nozzle array 7, the splitting zone, and ribbon spreader 5 to separate the tow into the desired ribbons FB in a continuous basis. The pneumatic splicing of the reconstituted individual filament bundles can be accomplished using known devices and techniques (such as one described by U.S. Pat. No. 4,803,762 and hereby incorporated by reference) for manufacturing convenience. The guide array 3 need only be restored in the event that the tow needs to be restarted. The dissociation pattern can be a rectangular or circular pattern, depending on the false twist nozzle array 7.

Processing fluids or gases are used to partially open and evenly or intermediately distribute processing aids into or on to the fiber ribbon or bundle. It is anticipated that the aids can be loosely held within the fiber ribbon or attached to the surface of single filament or multiple filaments for various purposes.

An advanced finish nozzle 10 (AFN) and other similar devices using laminar or turbulent flow around or through the advancing filament ribbon or bundle can also be used to uniformly and evenly disperse processing aids on the advancing fiber ribbons to further maintain bundle cohesion. One example of a suitable AFN is a low pressure finish application air nozzle (such as one described in U.S. Pat. No. 6,526,739 and hereby incorporated by reference) comprising a filament bundle passageway having a chamber, a plurality of compressed air delivery orifices opening into the chamber, and a plurality of finish delivery orifices that open into the chamber and positioned to apply a processing aid.

Suitable examples of processing aids include application of thermoset polyurethane (TPU) in a suitable suspension or other processing aids (sealants or lubricants etc.) that may be cured "in line" by IR heating in an oven 12 or by the additional application of reactive chemistries. Tension control rolls 15 maintain precise tension control of the advancing carbon fiber ribbon. The application of a discrete marker particle applied in a continuous pattern or a discontinuous pattern for the purpose of identifying or marking the processed carbon fiber may also be desirable.

Once the processing aids are applied, the ribbons are then wound onto respective take-up tubes or bobbins using carbon fiber ribbon winders 14. Use of a circular aperture between the rolls 15 and winders 14 may help to reduce tension spikes in the advancing filament bundles. Factors such as the helix angle and winding tension can be modified as the ribbon is wound. The use of a fan-based or pneumatic (meaning compressed air driven) material handling device may be required to adroitly manage the sub tow fiber ribbons in the process apparatus.

The carbon fiber ribbon splitting apparatus described herein may be employed for continuous processing, presuming that the direct feed of the carbon fiber ribbon (bundle) is comprised of a single (meaning tow ribbon bundle) or multiple feeds of fiber wound on tubes or cones feeding into a carburizing process. The subsequent aggregated fiber tow exits a carburizing furnace into the false twist ribbon separator (CFRS) process technology represented by the process diagrams of FIG. 1 or 2A and 2B describing the apparatuses and equipment. The false twist nozzle can produce false twist patterns up to 100 Hertz, but the resultant fiber bundle has zero residual twist and preferably maintains its ribbon form instead of shaped fiber bundles (meaning round, oval or other).

Filament sensors 9, 11, 13 may be employed to verify even distribution of carbon fibers after dissociation of the carbon fiber tow. If the filament sensor 9 (or 11 or 13) determines that the reduced filament counts in filament bundles do not equal the desired filament count, one or more individual filaments from a filament bundle having a filament count higher than a desired filament count may be transferred to another filament bundle (for instance, by using a needle configured for transferring a filament between the separate filament bundles) having a filament count lower than the desired filament count to equalize the reduced filament counts. By way of example and not limitation, filament sensor 9 (or 11 or 13) may apply an electrical current to measure electrical resistance of the advancing filament bundle. The electrical load applied to the advancing fiber bundle will be intrinsically safe. As seen in an example in FIGS. 6A and 6B, a segment of a bundle or tow of filaments is connected to a data acquisition system to collect resistance measurements over time. One or more filament sensors 9, 11, 13 may be used along various stages of the process. For example, filament sensor 9 or 11 or 13 may be used to verify the filament count of the re-bundled ribbons.

Figure 6B:
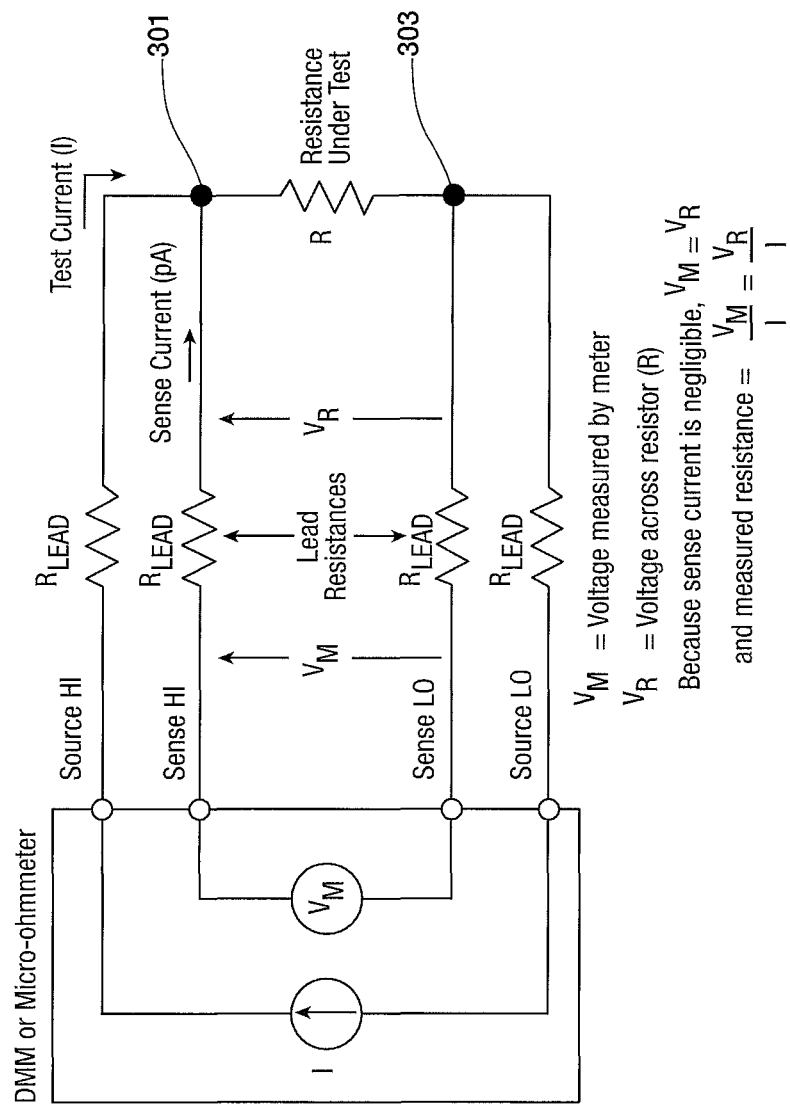
FIG. 6B is a schematic of the electrical circuit of the fiber sensor.

The sensor setup can be as shown in FIGS. 6A and 6B, with FIG. 6A being a visual representation of a prototype sensor set up and FIG. 6B a schematic. The tow or bundle of filaments under test is passed over contacts 301 and 303 a fixed distance apart. Applying a uniform tension to the fiber bundle(s) between 301 and 303 enables repeatable characterization of the fiber bundles; for example, about 150 grams, or as required, for stable measurements.

An electrical current I is passed through the segments to tow or ribbon under test and the voltage $V_M$ drop across the contacts 301 and 303 is measured. Alternatively, a fixed voltage $V_M$ can be applied across the electrodes, with the resulting current as a variable. Either way, the sensed resistance is determined as $V_M/I$. For a setup where a tow is being split into four reduced filament count bundles, each of the four reduced filament count bundles has its own sensor of this sort, so the measurements can be compared. The contacts 301 and 303 are arranged so that the tow or bundle of filaments to be tested makes contact continuously as the tow or bundle advances, so that the filament counts of the process can be continuously monitored. The segment under test changes as the filaments advance.

Figure 7A:
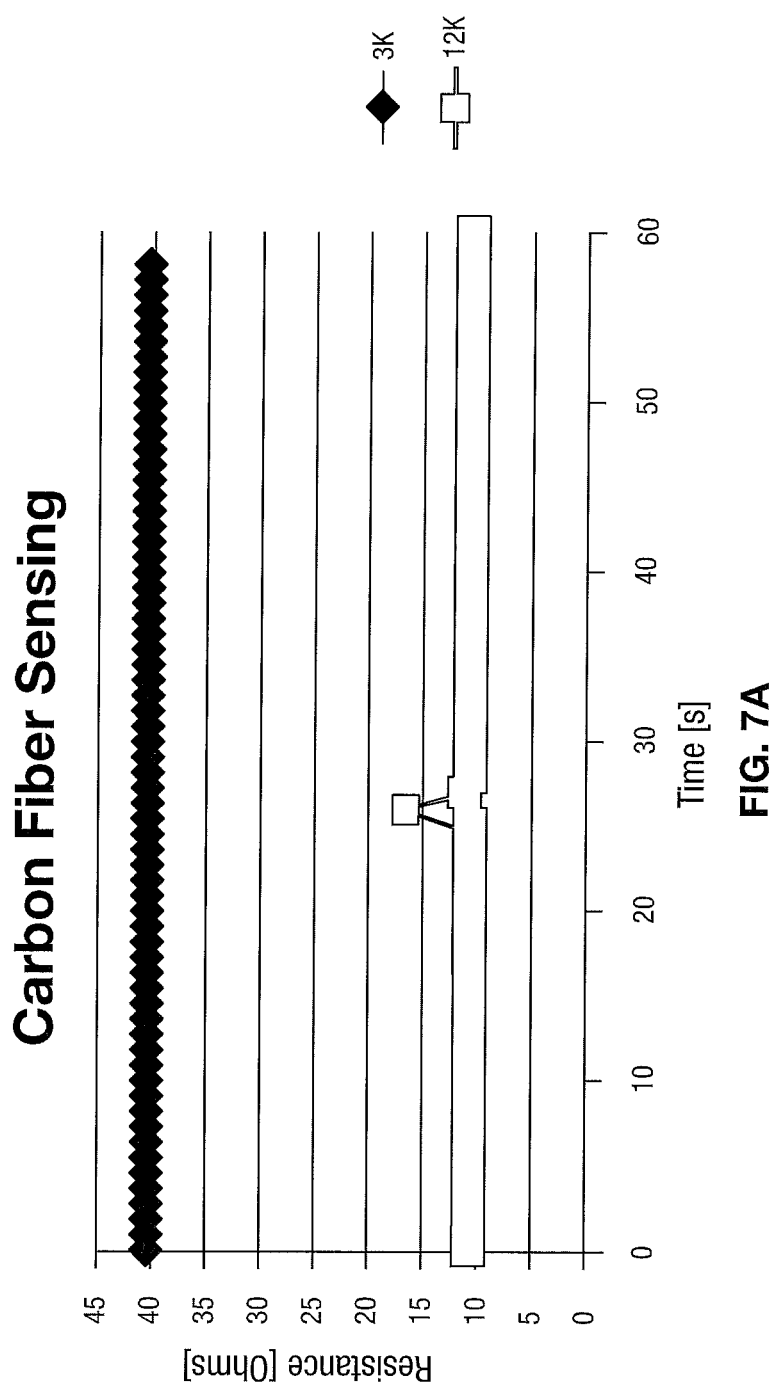
FIG. 7A is a time-series plot of electrical resistance for various carbon filament bundles.
Figure 7B:
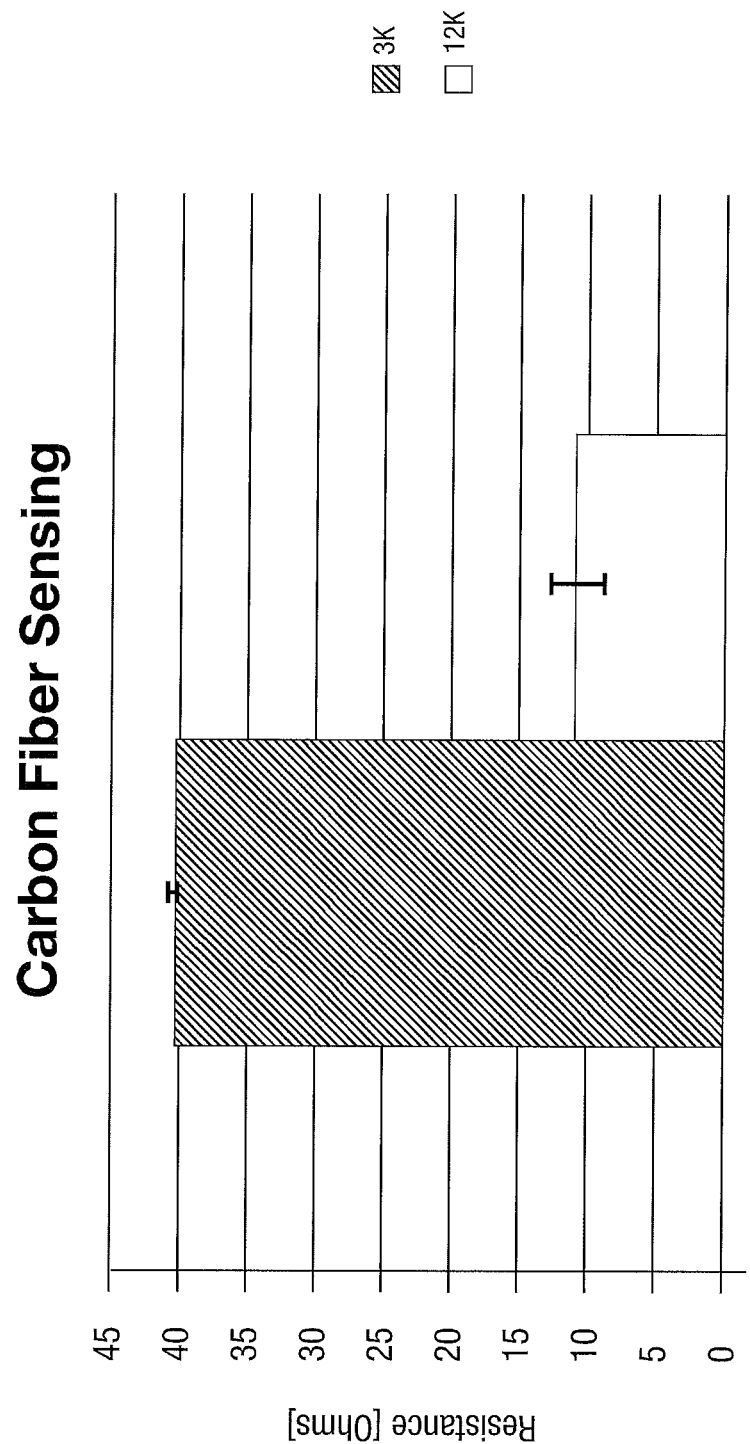
FIG. 7B is a bar chart comparing the electrical resistance for various carbon filament bundles.

Carbon filament bundle weight and resistance were statistically evaluated for two different sized bundles (12K and 3K). Electrical resistance measurements were made across a 12 in (30.48 cm) length. FIGS. 7A and 7B depict comparisons of the electrical resistance between 12K carbon filament bundles and 3K carbon filament bundles. The resistance measurements proved to deliver stable and reliable measurement of the carbon filament bundle size. The data indicates a ¼ reduction of the carbon filament bundle size increases carbon filament bundle resistance by a factor of 4.

Other forms of filament sensors 11 may be used, such as for identifying fluorescing optical particles and uniformity of distribution on the advancing filament ribbon. For example and not by way of limitation, filament sensor 9 or 11 may employ filament movement sensing. In another example, filament sensors 9 or 11 may optically measure light from the advancing bundles for purposes such as product tracking. It is expected that using a particle responding to the UV spectrum could be a suitable technique for product identification purposes. For example, a fluorescing particle applied in an aqueous solution could be mechanically trapped, mechanically attached within, or on the surface of a processed fiber ribbon (bundle). An example would be a commercially available fluorescing optical brightener (BASF Untex) or other particle(s) applied at levels that can be detected, but not limit fiber surface wetting and adhesion by resins. The examples could be used to identify processed carbon fiber for run time duration (fiber length), for time-metered winding, or unwinding in downstream processes, to identify unauthorized users of the CFRS-processed fiber and or to identify specifically marked carbon fiber ribbons in fabrics (etc.) as a measure of liability protection against false claims.

Figure 8:
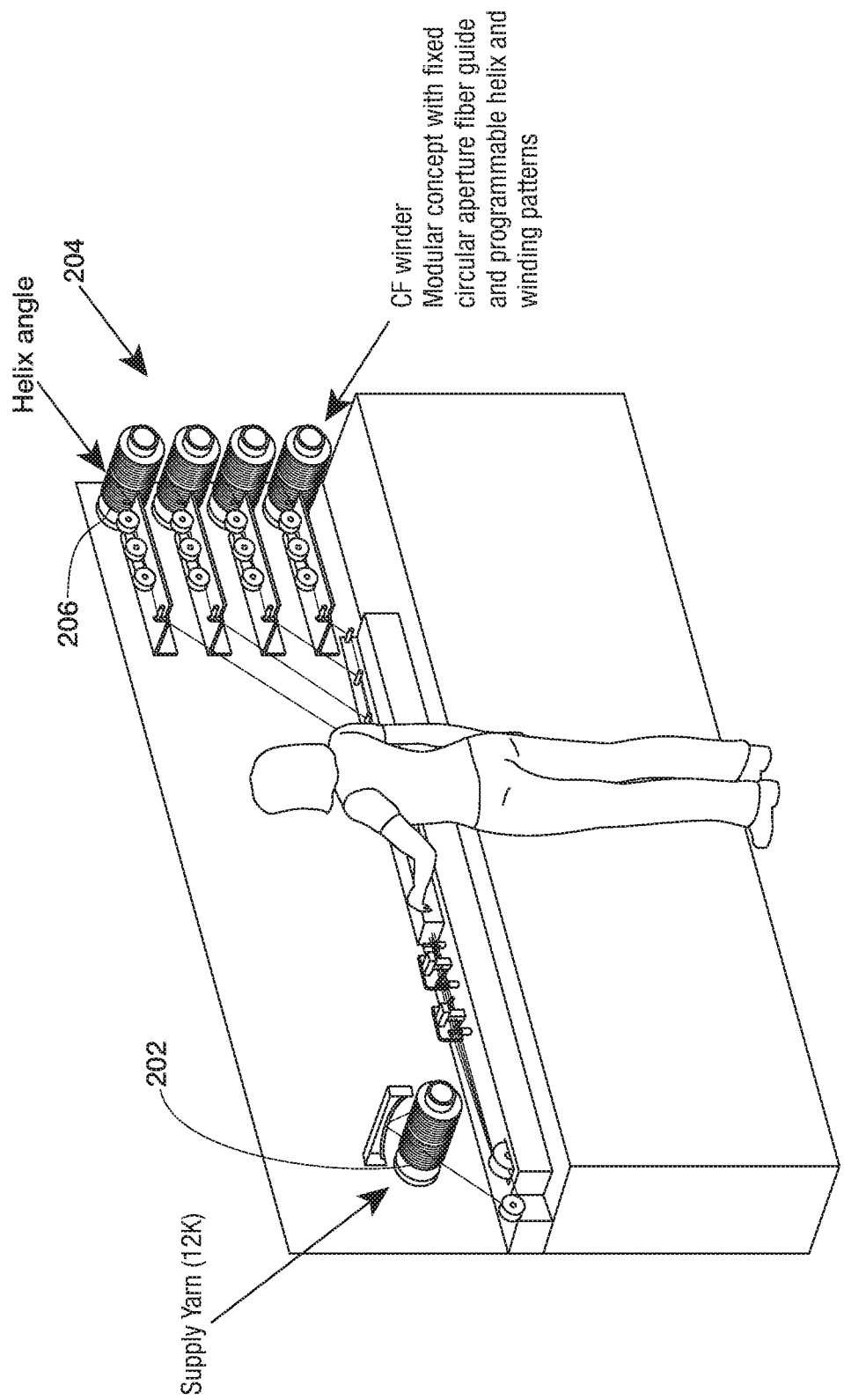
FIG. 8 is an overview of a discontinuous carbon fiber ribbon (CFRS) separator and process according to one embodiment.

FIG. 8 shows another embodiment wherein the carbon fiber splitting apparatus is a discontinuous carbon fiber ribbon (CFR) splitter. A discontinuous splitting process presumes the direct feed of the carbon fiber ribbon (bundle) from a wound tube of supply fiber 202 under controlled tension (electronically adjustable with monitoring software) into the false twist carbon fiber ribbon (CFRS) splitting processing equipment. The false twist nozzle can produce false twist patterns up to 100 Hertz, but with the resultant fiber bundle having zero residual twist and maintaining its ribbon form instead of shaped fiber bundles (meaning round, oval or other).

The resultant multi-ribbons are maintained as separate fiber ribbon entities and subsequently wound as a group on winder tubes 204 (meaning two or more) or individually on separate winder mandrels. These winders are grouped in vertical or horizontal patterns that facilitate a nearly straight fiber path and a tension-stable fiber ribbon geometry path. The fiber ribbons are each passed through a fixed (meaning a non-reciprocating) circular or arch segment aperture guide 206 facilitating their winding onto a take-up without interfering with the dissociation process upstream. The aperture guide 206 includes a suitable diameter and perimeter fiber entry and exit radius shapes to support the advancing fiber ribbon, and prevents random 180 degree rotations (meaning turning of the fiber ribbon on itself) during the winding process by keeping the re-bundled ribbon flat and reducing tension spikes as it is wound onto the take-up.

The advancing fiber ribbons are supported on a low-friction surface (circular or arch segment) of the aperture 206 during the winding process. The advancing fiber ribbon is in constant contact with a supporting aperture surface and is allowed to reciprocate approximately 180 degrees during the winding process while maintaining constant contact in ribbon form as it is wound on a tube in the desired pattern. The winders 204 can be arranged vertically, curved or in another pattern to facilitate fiber ribbon winding.

Since the aperture guides 206 remain fixed, the winders 204 are configured to reciprocate as the ribbon is wound onto the take-up winders. The winders 204 may be mounted to a reciprocating support as a group of winders (meaning that the winders are synchronized in their movement as a group of winders). The group of winder spindles are synchronized (with respect to the revolutions per minute and winding start time initiation). This process is applicable for use with a fiber winding apparatus where the fiber geometry path is horizontally or otherwise presented to fixed fiber support guides to the multiple winders. The winder stack is reciprocated (along the take up tube's longitudinal axis) in the desired winding pattern length while the tube is rotated to provide the desired helical fiber lay pattern. For example, the re-bundled ribbon may wound in a harmonic pattern (e.g., in a "FIG. 8" pattern) as the tube reciprocates along an axis. The winders 204 may reciprocate independently of one another and need not reciprocate in phase with one another.

In some embodiments, multiple fiber ribbons may be wound onto a single take-up. The separated ribbons are passed through the circular apertures 206 concurrently (meaning side by side) while retaining their individual ribbon integrity. The ribbons (2 or more) are then wound and layered in a helical pattern on the winder mandrel. Custom winding patterns may be used to facilitate the multiple ribbon winding and ribbon layering for tube stability and subsequent processing. Precise winding tensions prevent the fiber from unintendedly winding or unwinding.

For example, two separate fiber ribbons may be wound to form a single tow of carbon fibers comprising a first 3K ribbon wound at a helix angle between about 20-30 degrees and a second 3K ribbon with approximately the same angles with for the adjacent fiber ribbons. The winding angle is reduced incrementally from 30 to 0 degrees as the fiber reaches the last 12-18 mm of each end of the winding pattern. These angles may be varied to create profiles that prevent the fiber ribbon(s) from "rolling" off the edge of the wound fiber layers, which create tension instability in weaving, braiding etc. In some examples, the fiber ribbons may have a winding tension between about 150-250 grams.

The present invention may also be considered as a method for splitting carbon fiber tows. In some embodiments, the carbon fiber splitting methods may be used to split a 12K carbon filament tow into reduced filament count bundles with a reduced filament count of 3K each. For example, one method for separating a 12K carbon filament tow into a set of 3K carbon filament tows may comprise feeding a ribbon from a 12K tow of carbon filaments into a guide array using a set of rollers to maintain constant tension of the ribbon and mechanically split within the guide array into a plurality of filament bundles each comprised of individual filaments. For a continuous process, the guide array may be moved such that the guide array does not contact the tow of carbon filaments. The reduced filament count tows are subjected to false twisting, such as in an air jet false twist nozzle array. With the guide array 3 removed, the false twist nozzle array loosens the filaments from one another and allows them to travel their separate paths.

False twists are applied to the filament bundles using a pneumatic false-twist nozzle array to loosen individual filaments in the filament bundles. The individual filaments of each filament bundle are then recombined into a 3K re-bundled ribbon utilizing the linear inter-filament friction of the filaments. Tension control of the re-bundled ribbons is maintained using tension control rolls and/or tension-controlled take-up winders.

The electrical resistance of advancing segments of each filament bundle can be measured to verify even distribution of carbon filaments. If the electrical resistances of the filament bundles are unequal, one or more individual filaments are transferred from one filament bundle having a lower resistance to another filament bundle having a higher resistance to equalize the electrical resistances and evenly distribute the carbon filaments. To facilitate dissociation, a ribbon coating may be at least partially removed from the filament bundles. The filament bundles are then fed into a guide pin assembly so the separated filament bundles take paths different from one another.

One or more coatings may be applied to each re-bundled ribbon to maintain bundle cohesion, and can be cured by infrared heating, such as by feeding the re-bundled coated ribbons through an infrared heating oven. Each cured re-bundled ribbon is wound onto a take-up to form a set of 3K carbon filament tows.

Other divisions of large number tows can be accomplished within the scope of the invention by using the appropriate number of guide arrays, false twist nozzles and the like. For example, a 12K tow can be divided into three 4K bundles, or six 2K bundles, or one 6K bundle and two 3K bundles. A 14K bundles can be divided into four 3.5K bundles. Other number combinations are also possible within the scope of this invention.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A method for separating a carbon filament tow into reduced filament count bundles comprising:
   feeding a tow of carbon filaments with a first filament count into a guide array using a set of rollers to maintain tension on the tow;
   mechanically splitting the tow within the guide array into a plurality of filament bundles with a reduced filament count;
   feeding the filament bundles into a guide pin assembly to separate the filament bundles with a reduced filament count from one another;
   applying a false twist to the filament bundles to loosen individual filaments in the filament bundles;
   recombining the individual filaments of each filament bundle into a re-bundled ribbon;
   winding each re-bundled ribbon onto a take-up,
   wherein the re-bundled ribbons have a reduced filament count that is lower than the first filament count.

2. The method of claim 1, wherein the first filament count is 12K.

3. The method of claim 2, wherein the reduced filament count is 3K.

4. The method of claim 1 further comprising determining a number of individual filaments in each re-bundled ribbon using a fiber sensor.

5. A method for separating a carbon filament tow into reduced filament count bundles comprising:
   feeding a tow of carbon filaments with a first filament count into a guide array using a set of rollers to maintain tension on the tow;
   mechanically splitting the tow within the guide array into a plurality of filament bundles with a reduced filament count;
   feeding the filament bundles into a guide pin assembly to separate the filament bundles with a reduced filament count from one another;
   applying a false twist to the filament bundles to loosen individual filaments in the filament bundles;
   recombining the individual filaments of each filament bundle into a re-bundled ribbon;
   winding each re-bundled ribbon onto a take-up,
   wherein the re-bundled ribbons have a reduced filament count that is lower than the first filament count,
   further comprising determining a number of individual filaments in each re-bundled ribbon using a fiber sensor and
   when the fiber sensor determines that the reduced filament counts in the re-bundled ribbons do not equal the desired filament count, transferring one or more individual filaments from a re-bundled ribbon having a filament count higher than a desired filament count to another re-bundled ribbon having a filament count lower than the desired filament count.

6. The method of claim 4, wherein the fiber sensor determines the number of filaments in each re-bundled ribbon by measuring the electrical resistance of the re-bundled ribbon.

7. The method of claim 4, wherein the fiber sensor determines the number of individual filaments in each filament bundle by measuring an optical characteristic of the filament bundle.

8. The method of claim 1, wherein applying the false twist to the filament bundles comprises using a pneumatic false twist nozzle array adapted to produce false twists at a frequency up to 100 Hz.

9. The method of claim 1, further comprising at least partially removing a coating from the filament bundles to facilitate dissociation.

10. The method of claim 9, wherein removing the coating is performed by applying processing aids.

11. The method of claim 10, wherein removing the coating comprises removing thermoset polyurethane from the filament bundles.

12. The method of claim 11, wherein removing the coating is performed using ultrasonic low sonication.

13. The method of claim 1, further comprising applying a second coating to each re-bundled ribbon to maintain bundle cohesion.

14. The method of claim 13, wherein applying the second coating to each re-bundled ribbon comprises applying thermoset polyurethane to the re-bundled ribbons.

15. The method of claim 1 further comprising curing the second coating by feeding the re-bundled ribbons through an infrared heating oven.

16. The method of claim 1 further comprising defining a helix angle formed between an advancing re-bundled ribbon and a plurality of ribbons wound on the take-up as the re-bundled ribbon is wound onto the take-up.

17. The method of claim 1 further comprising adjusting a winding tension before winding the re-bundled ribbon onto the take-up.

18. The method of claim 1 further comprising maintaining tension control of the re-bundled ribbons using tension control rollers.

19. The method of claim 1, wherein recombining the individual filaments of each filament bundle into a re-bundled ribbon includes utilizing linear inter-filament friction of the individual filaments.

* * * * *